United States Patent [19]

Pless

[11] Patent Number: 5,531,765
[45] Date of Patent: *Jul. 2, 1996

[54] METHOD AND APPARATUS FOR PRODUCING CONFIGURABLE BIPHASIC DEFIBRILLATION WAVEFORMS

[75] Inventor: Benjamin D. Pless, Atherton, Calif.

[73] Assignee: Ventritex, Inc., Sunnyvale, Calif.

[*] Notice: The term of this patent shall not extend beyond the expiration date of Pat. No. 5,352,239.

[21] Appl. No.: 275,852

[22] Filed: Jul. 15, 1994

Related U.S. Application Data

[63] Continuation-in-part of Ser. No. 37,482, Mar. 24, 1993, Pat. No. 5,352,239, which is a continuation of Ser. No. 629,252, Dec. 18, 1990, abandoned.

[51] Int. Cl.$^6$ .................................................. A61N 1/39
[52] U.S. Cl. .................................................. 607/5
[58] Field of Search ................................ 607/5, 6, 7, 8

[56] References Cited

U.S. PATENT DOCUMENTS 4,708,145  11/1987  Tacker, Jr. et al. ................... 607/5
4,996,984  3/1991  Sweeney ................................. 607/5

*Primary Examiner*—William E. Kamm
*Assistant Examiner*—Scott M. Getzow
*Attorney, Agent, or Firm*—Steven M. Mitchell; Mark J. Meltzer

[57] ABSTRACT

A programmable implantable medical device utilizable for delivering a configurable defibrillation waveform to a patient's heart. The device includes defibrillation electrode means adapted to be connected to the heart for delivering a multiphasic defibrillation waveform thereto. A programmable waveform generator connected to the heart generates the biphasic waveform such that the first phase of the defibrillation waveform has programmed tilt and the second phase has a duration which is a function of the duration of the first phase.

2 Claims, 3 Drawing Sheets

METHOD AND APPARATUS FOR PRODUCING CONFIGURABLE BIPHASIC DEFIBRILLATION WAVEFORMS

This application is a continuation-in-part of application Ser. No. 08/037,482 filed Mar. 24, 1993, now U.S. Pat. No. 5,352,239, which is a continuation of application Ser. No. 07/629,252 filed Dec. 18, 1990, now abandoned.

FIELD OF THE INVENTION

The present invention relates to implantable medical devices and, in particular, to a programmable defibrillator capable of delivering a configurable biphasic waveform.

BACKGROUND OF THE INVENTION

Implantable defibrillators use truncated exponential waveforms to defibrillate the heart. The earliest devices used monophasic waveforms. More recent clinical investigations have evaluated the increased effectiveness of biphasic waveforms. See Troup, Implantable Cardioverters and Defibrillators, Current Problems in Cardiology, Volume XIV, Number 12, Dec. 1989, pages 729–744. Some investigators have even recommended the use of triphasic waveforms as the most effective waveform for defibrillating a heart. See U.S. Pat. No. 4,637,397 issued to Jones and Jones on Jan. 20, 1987.

As described by Troup, monophasic waveforms are typically produced using silicon controlled rectifier (SCR) technology that truncates the pulse by "dumping" the energy on the defibrillator capacitor. This leaves no energy available on the capacitor for producing multiphasic waveforms. As further described by Troup, there have been two methods available for truncation of a monophasic defibrillation waveform. According to one method, pulse truncation is accomplished by comparing the capacitor voltage to a reference voltage which is usually chosen as a function of the waveform leading edge voltage. The result is a defibrillation pulse with a constant ratio of trailing edge to leading edge voltage, or a "constant tilt" pulse.

Defibrillation pulse "tilt", described as percent tilt, is defined as follows:

$$\%Tilt = 100[1-(V_f/V_i)]$$

where $V_f$ is the trailing edge voltage of the pulse and $V_i$ is the leading edge voltage.

According to the second method, the defibrillation pulse is truncated by a timing circuit so that the pulse duration is constant. Biphasic waveform generators have used MOS switches to produce the defibrillator output. The MOS switch technique is better suited to multiphasic waveforms since the defibrillator capacitor does not need to be "dumped" to truncate the pulse.

Prior art biphasic waveforms have been programmable in terms of pulse duration. The disadvantage of programming biphasic waveforms in terms of duration can be seen in FIG. 1. Panel 1 of FIG. 1 shows a conventional biphasic waveform with a 50 ohm load. Panel 2 shows a conventional biphasic waveform with the same duration of phases with a 25 ohm load. With a 50 ohm load, there is adequate residual voltage to produce an effective negative phase of the biphasic waveform. However, at the same pulse durations, with a 25 ohm load, the voltage during the positive phase has decayed to the point where very little is left for the negative phase.

While it is possible to select optimal pulse durations for a given patient impedance, the patient impedance may change. In particular, for higher defibrillation voltages, the patient impedance is lower. In addition, over time, the lead impedance may increase due to the build-up of scar tissue.

Due to their small size and battery operation, implantable defibrillators have limited output energy capability. It is not unusual for an implantable defibrillator to have only slightly more output capability than is required to defibrillate a patient. This lack of safety margin makes it all the more important that the output energy that is available is used in the most effective manner. While biphasic waveforms are a step in the right direction, the optimal settings for the positive and negative phase durations have not been addressed in the prior art.

U.S. Pat. No. 4,850,357 issued to Stanley M. Bach, Jr. on Jul. 25, 1989, discloses a circuit for generating a biphasic defibrillation waveform wherein both the positive and negative phases have constant tilt. However, the Bach, Jr. defibrillator generates a biphasic waveform having fixed characteristics. That is, only a single type of waveform can be delivered that has a first positive pulse having a specified constant tilt and a second negative pulse also having a specified constant tilt. Thus, the Bach defibrillator circuit provides none of the therapeutic flexibility that is desirable in restoring rhythm to a fibrillating heart.

SUMMARY OF THE INVENTION

The present invention provides a microprocessor controlled output stage that allows for greater flexibility than has been available in defining a biphasic defibrillation waveform. In accordance with the invention, the biphasic waveform generator may be programmed to provide a positive phase having a selected tilt and a negative phase having a duration that is related to the duration of the positive phase. The disclosed apparatus can also produce conventional multiphasic waveforms, if desired.

The invention further defines a method for delivering a configurable biphasic waveform. A capacitor or capacitor bank is charged to an initial selected voltage. A first defibrillation pulse of a first polarity is delivered to the heart and the capacitor voltage is monitored. When the voltage of the capacitor decays to a programmed decay voltage, the first pulse is discontinued and the duration of said first defibrillation pulse is measured. Delivery of a second defibrillation pulse of a second polarity is initiated and then discontinued at a time which is a function of the measured duration of the first defibrillation pulse.

A better understanding of the features and advantages of the present invention will be obtained by reference to the following detailed description and accompanying drawings which set forth an illustrative embodiment in which the principles of the invention are utilized.

DETAILED DESCRIPTION OF THE INVENTION

The invention is directed to programmable control circuitry for an implantable defibrillator output stage that generates configurable biphasic defibrillation waveforms having selected tilt of a first pulse and a second opposite polarity pulse having a duration which is a function of the duration of the first pulse. In the disclosed embodiment, the defibrillator has an on-board microprocessor and the control circuitry acts as a peripheral to the microprocessor.

Figure 1:
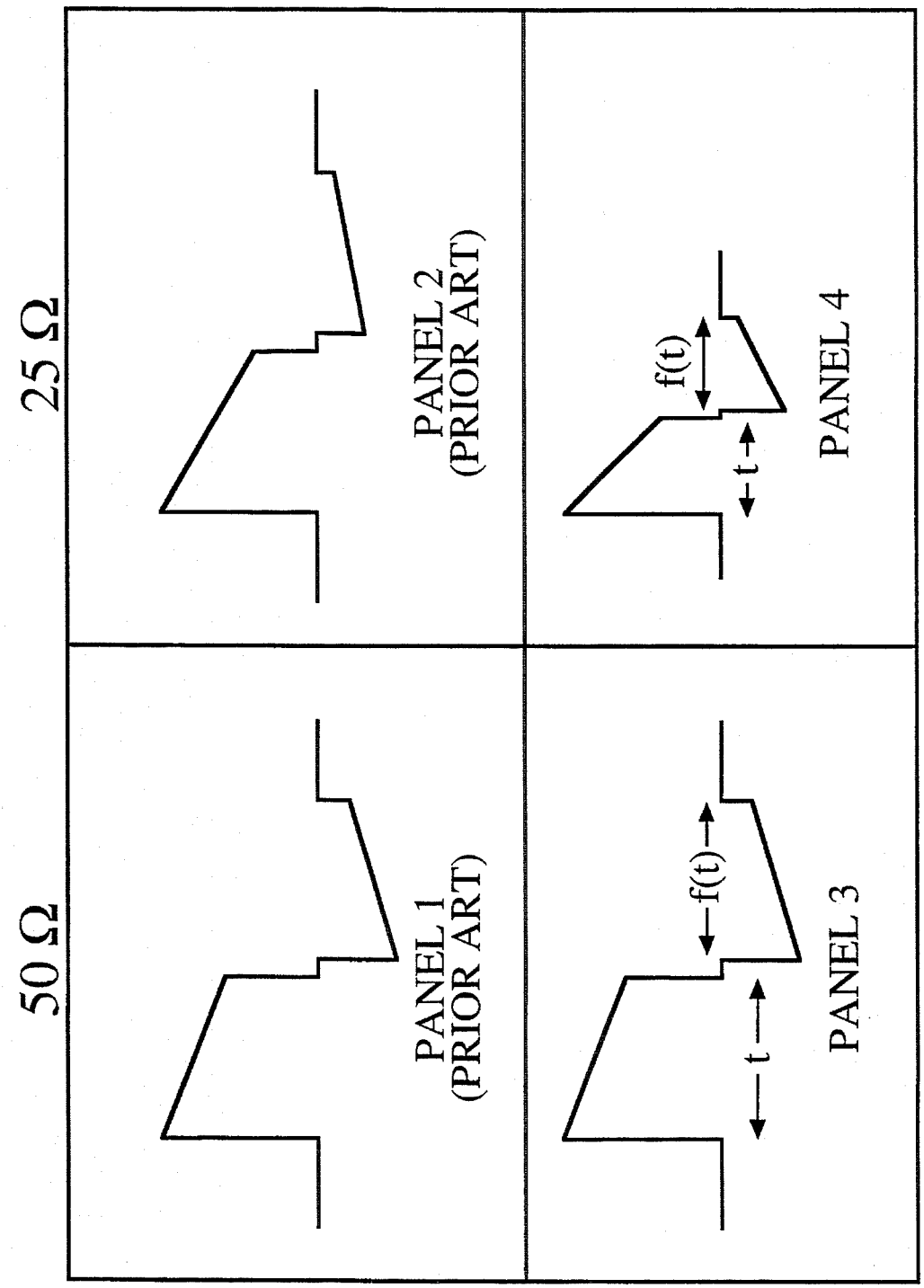
FIG. 1 provides a comparison between prior art biphasic waveforms and configurable biphasic waveforms generated in accordance with the present invention.

With a biphasic waveform, where the first phase has a constant tilt and the second phase has the same duration as the first phase, sufficient voltage for the negative phase is assured, as shown in panels 3 and 4 of FIG. 1. Panel 3 shows a constant tilt first pulse biphasic waveform with a 50 ohm load and with a duration of time t and a second pulse which has a duration which is a function f(t) of the first pulse. Panel 4 shows a biphasic waveform with the same constant tilt first pulse with a 25 ohm load wherein the duration of the pulse is shorter for both pulses. In these examples, f(t)=t. The initial voltage on the biphasic waveform generated by the apparatus of the invention is the same in both cases.

With a multiphase constant tilt defibrillation waveform, the duration of each phase of the waveform is dependent upon the patient impedance. Some studies (Tang, et al., Ventricular Defibrillation Using Biphasic Waveforms: The Importance of Phasic Duration, JACC Vol. 13, No. 1, January 1989) support the idea that the relative durations of the phases of a biphasic waveform are important in determining its efficacy. Therefore, it is desirable to be able to measure the duration of the first, constant tilt phase of a biphasic waveform and then set the negative phase duration to some percentage of the measured positive phase duration. Mathematical functions other than a straight percentage could be used. This provides the ability to optimize biphasic waveform durations.

Figure 2:
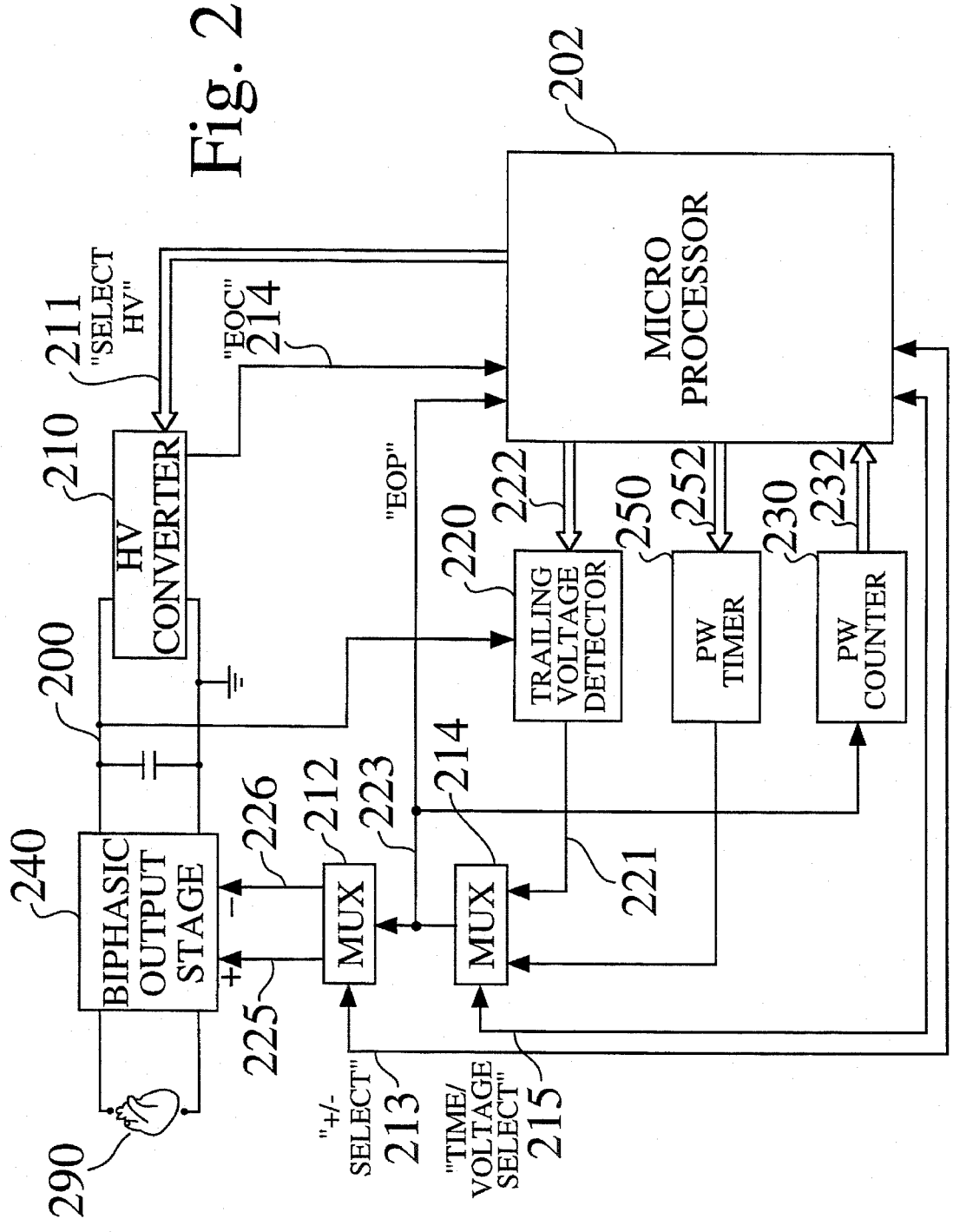
FIG. 2 is a block diagram illustrating an embodiment of an apparatus for generating a configurable, biphasic waveform in accordance with the present invention.

Referring to FIG. 2, in the illustrated embodiment of the invention, a control system is used which comprises functional modules and addresses that the microprocessor can read from or write to.

Figure 3:
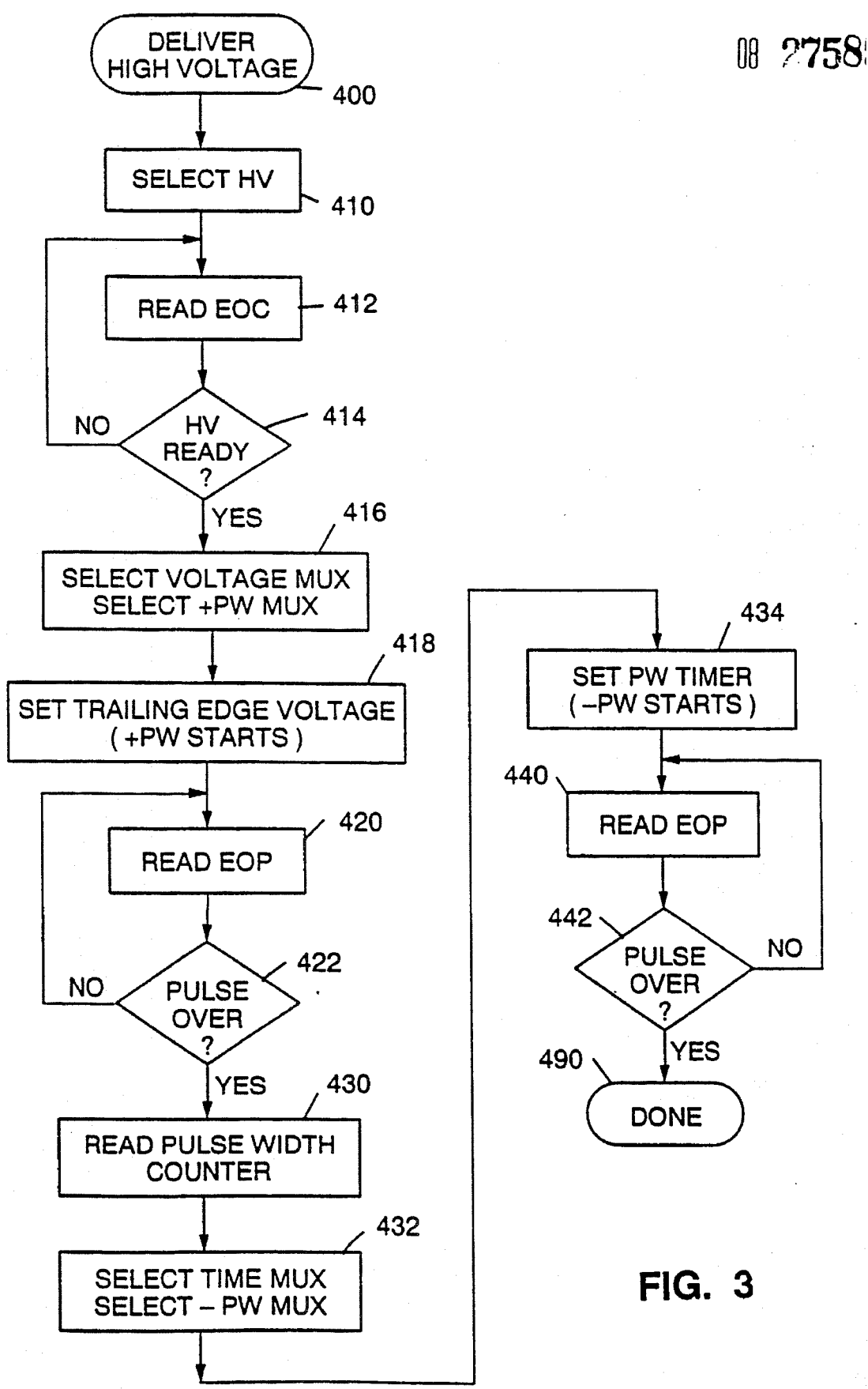
FIG. 3 is a flow chart of a method for producing a biphasic waveform with a selected constant tilt positive phase and a negative phase the duration of which is a function of to the duration of the measured positive phase duration.

FIG. 3 is a flow diagram that will be used in conjunction with the FIG. 2 block diagram to describe how a biphasic waveform having a positive pulse of selected constant tilt and a negative pulse duration which is a function of the positive pulse duration can be generated.

At step 400, the microprocessor 202 decides that a defibrillation output is necessary. Before a pulse can be delivered, however, energy must be stored on the defibrillation capacitor 200, which typically has a value of about 150 microfarads. At step 410, the microprocessor 202 addresses the high voltage converter 210 to command it to start charging the defibrillation capacitor 200 to the selected initial voltage (address "select HV" 211).

At step 412, the microprocessor 202 starts a polling loop by reading "EOC" 214. "EOC" is the end-of-convert signal from the high voltage converter 210 and signifies that the converter has finished charging the capacitor 200 to the selected voltage. After reading "EOC" at step 412, the microprocessor 202 determines if the high voltage is ready at 414.

If the high voltage is not ready, then the microprocessor 202 loops back to step 412. In some implementations, it may be desirable for the microprocessor 202 to attend to other tasks or to be disabled for periods to conserve current during polling loops. If, at step 414, the microprocessor 202 finds that the defibrillator capacitor 200 is charged to the selected initial voltage, then the defibrillator system is prepared for delivery of a positive pulse. The pulse width is determined by the length of time required for the defibrillator capacitor to decay to a selected decay voltage. If, in this illustrative example, the selected peak voltage is 500 volts, then 200 volts would be a reasonable target voltage for the trailing edge voltage of the positive pulse to assure an effective negative phase.

At step 416, the microprocessor manipulates the controls of two multiplexers to set the output stage to terminate the pulse when the selected trailing edge is detected on the defibrillation capacitor 200. Multiplexer 212 selects the signal flow to either generate a positive pulse or a negative pulse. At step 416, the microprocessor 202 addresses "± select" 213 to choose a positive pulse. Multiplexer 214 selects the signal flow to either produce a pulse with a timed duration or a pulse which terminates when a selected decay voltage is detected on the defibrillator capacitor 200. At step 416, the microprocessor 202 addresses "time/voltage select" 215 to choose a pulse which terminates when a selected decay voltage is detected.

The positive pulse is started by the microprocessor 202 at step 418 by addressing "trailing voltage select" 222 and setting the selected trailing edge voltage to 200 volts (in this example). Since the voltage on the defibrillator capacitor 200 is at 500 volts, the output 221 of the trailing voltage detector 220 goes high. This signal 221 goes through multiplexer 214 to line 223 and through multiplexer 212 to the positive pulse input 225 of the biphasic output stage 240 which generates a positive defibrillation output as long as positive pulse input 225 is asserted.

Once the positive pulse is started, the voltage on the defibrillator capacitor starts to decline as current flows into the patient's heart 290. Trailing voltage detector 220 maintains signal 221 high until the voltage on the defibrillator capacitor 200 has decayed to less than the trailing voltage selected by address 222. In this example, when the capacitor voltage decays to 200 volts, the trailing voltage detector 220 responds by forcing its output 221 low. This signal goes through 214, 223, and 212 to the positive pulse input control 225 of the biphasic output stage 240, terminating the positive pulse.

While the positive pulse is being generated, the microprocessor waits in a polling loop for the pulse to end. The microprocessor 202 reads "EOP" at step 420. "EOP" is the end-of-pulse signal and is the same as line 203 discussed above. As long as the pulse is being generated, "EOP" is high; when the pulse is over "EOP" goes low. Having read "EOP" at step 420, the microprocessor 202 checks to see if the pulse is over at step 422. If the pulse is not over, then the microprocessor loops back to step 420. When the positive pulse ends, the microprocessor sets up the hardware to produce the negative pulse which is to have a duration which is a function of the positive pulse (in this example, the negative pulse will be set equal in duration to the positive pulse).

Since the positive phase pulse was terminated by the capacitor 200 reaching a selected decay voltage (200 volts in this example), the pulse duration is dependent upon the impedance of the patient's heart. For example, a comparatively low impedance of 25 ohms would result in a shorter pulse duration of about 3.4 milliseconds (for a 150 microfarad capacitor 200), while a 50 ohm patient impedance would result in a pulse duration of 6.8 milliseconds.

Once the positive pulse is over, at step 430 the microprocessor 202 addresses the pulse width counter 230 (address "pulse width read" 232) to determine the positive phase pulse duration. The pulse width counter 230 measures the duration of "EOP" 223. Thus, the address "pulse width read" 232 contains the duration of the positive pulse. The microprocessor 202 stores the duration of the positive pulse width for future use.

At step 432, the microprocessor 202 manipulates the controls of two multiplexers 212 and 214 to set the output stage to produce a negative pulse with a timed duration. Multiplexer 212 selects the signal flow to either generate a positive pulse or a negative pulse. At step 432, the microprocessor 202 addresses "± select" 213 to choose a negative pulse. Multiplexer 214 selects the signal flow to either produce a pulse with a timed duration or a pulse which terminates when a selected decay voltage is detected on the defibrillator capacitor 200. At step 432 the microprocessor 202 addresses "time/voltage select" 215 to choose a pulse with a timed duration.

The negative pulse is started by the microprocessor 202 at step 434 by writing to the pulse width timer 250 at address "pulse width select" 252. The pulse width timer produces a pulse of a duration which the microprocessor 202 sets by writing a value to address "pulse width select" 252. In this example, the microprocessor makes the duration of the negative phase the same as the duration of the positive phase. To do this, the microprocessor 202 writes into the pulse width timer 250 the value of the positive phase duration which it read from "pulse width read" 232 and stored. If the microprocessor was to make the negative phase twice the duration of the positive phase, then the microprocessor would multiply by two the positive phase duration (which it read from "pulse width read" 232 and stored) before writing it into the pulse width timer 250. As should be clear, the negative phase duration can be made any mathematical function of the positive phase duration by manipulating the data representation of the positive phase duration read from "pulse width read" 232.

By writing to the pulse width timer 250, at step 434, the microprocessor 202 starts the negative pulse. The pulse width timer 250 produces a pulse the duration of which is set by the data the microprocessor 202 wrote to address "pulse width select" 252 (which is equal to the positive pulse duration read from address "pulse width read" 232 in this example). The pulse from the pulse width timer 250 passes through multiplexer 214 and multiplexer 212 to the negative pulse input 226 of the biphasic output stage 240. The biphasic output stage 240 applies the negative phase output to the heart 290 for as long as its input 226 is asserted.

While the negative pulse is being generated, the microprocessor waits in a polling loop for the pulse to end. The microprocessor 202 reads "EOP" at step 440. As long as the pulse is being generated, "EOP" is high; when the pulse is over, "EOP" goes low. Having read "EOP" at step 440, the microprocessor checks to see if the pulse is over at step 442. If the pulse is not over, then the microprocessor loops back to step 440. When the negative pulse ends, the microprocessor exits the program flow at step 490.

As should be apparent, many combinations of selected constant tilt and selected constant duration (or related duration) multiphasic waveforms can be produced under microprocessor control using the apparatus disclosed above.

Thus, it should be understood that various alternatives to the embodiments of the invention described herein may be employed in practicing the invention. It is intended that the following claims define the scope of the invention and that methods and apparatus within the scope of these claims and their equivalents to covered thereby.

What is claimed is:

1. An implantable medical device utilizable for delivering a configurable biphasic defibrillation waveform to a patient's heart, the medical device comprising:

(a) charge storage means;

(b) charging circuitry for charging the storage means to an initial selected voltage; and (c) control means for initiating delivery of a first defibrillation pulse of a first polarity to the heart after the storage means stores the initial selected voltage and for initiating delivery of a second defibrillation pulse of a second polarity to the heart when the voltage of the charge storage means decays to a programmed decay voltage, said control means including timer means for measuring the duration of said first pulse and for controlling the duration of the second pulse as a function of the duration of said first pulse.

2. A method for delivering a configurable biphasic defibrillation waveform from an implantable medical device to a patient's heart, comprising the steps of:

(a) charging a capacitor to an initial selected voltage;

(b) initiating delivery of a first defibrillation pulse of a first polarity to the heart after the capacitor stores the initial selected voltage;

(c) monitoring the voltage of said capacitor;

(d) discontinuing the delivery of said first defibrillation pulse when the voltage of said capacitor decays to a programmed decay voltage;

measuring the duration of said first defibrillation pulse;

(f) initiating delivery of a second defibrillation pulse of a second polarity; and (g) discontinuing the delivery of said second defibrillation pulse at a time which is a function of the measured duration of said first defibrillation pulse.

* * * * *